United States Patent [19]
Tsay et al.

[11] Patent Number: 5,510,465
[45] Date of Patent: Apr. 23, 1996

[54] HEAT-TREATED IGM ANTIBODY PREPARATIONS

[75] Inventors: Grace C. Tsay, Walnut Creek; Gary Jesmok, Pinole, both of Calif.

[73] Assignee: Bayer Corporation, Elkhart, Ind.

[21] Appl. No.: 96,398

[22] Filed: Jul. 26, 1993

Related U.S. Application Data

[62] Division of Ser. No. 504,161, Apr. 3, 1990, Pat. No. 5,256,771.

[51] Int. Cl.$^6$ .......................... C07K 16/06; A61K 39/395
[52] U.S. Cl. ...................... 530/389.1; 530/390.5; 424/130.1; 424/177.1
[58] Field of Search .............. 530/389.5, 389.1, 530/388.4, 388.2, 390.2; 424/85.8, 177.1, 730.1

[56] References Cited

U.S. PATENT DOCUMENTS 4,318,902  3/1982  Stephan .
5,190,752  3/1993  Möller et al. .

OTHER PUBLICATIONS

Haque et al. Am J Dis Child. 142: 1293–1296, 1988.
Wickerhauser et al. Vox Sang 23: 119–125, 1972.
Steinbach et al., Preparative Biochemistry 3: 363–373, 1973.
Barandun, et al., "Intravenous Administration of Human γ-Globulin", Vox. Sang., vol. 7, pp. 157–174 (1962).
Siegel, et al., "Effects of Limited Denaturation by Heat on the Dynamic Conformation of Equine Immunoglobulin M Antibody on the Interaction with Antigens and Complement", Biochemistry, vol. 10, pp. 192–198 (1981).

*Primary Examiner*—Paula K. Hutzell
*Attorney, Agent, or Firm*—James A. Giblin

[57] ABSTRACT

Mild heat-treatment of IgM antibody concentrates diminishes the potential to induce non-specific complement activation without significant loss of normal immunologic effector functions. These IgM immunoglobulin concentrates retain specific antigen binding properties and activate complement when bound to antigen. Preferred product includes at least 20% by weight IgM in an IgM/IgG antibody mixture. Heating is done at a temperature within the range of about 40° C. to 62° C., preferably about 45° to 55° C., in a solution having an acid pH (preferably 4.0 to 5.0) for at least about 10 minutes.

5 Claims, 3 Drawing Sheets

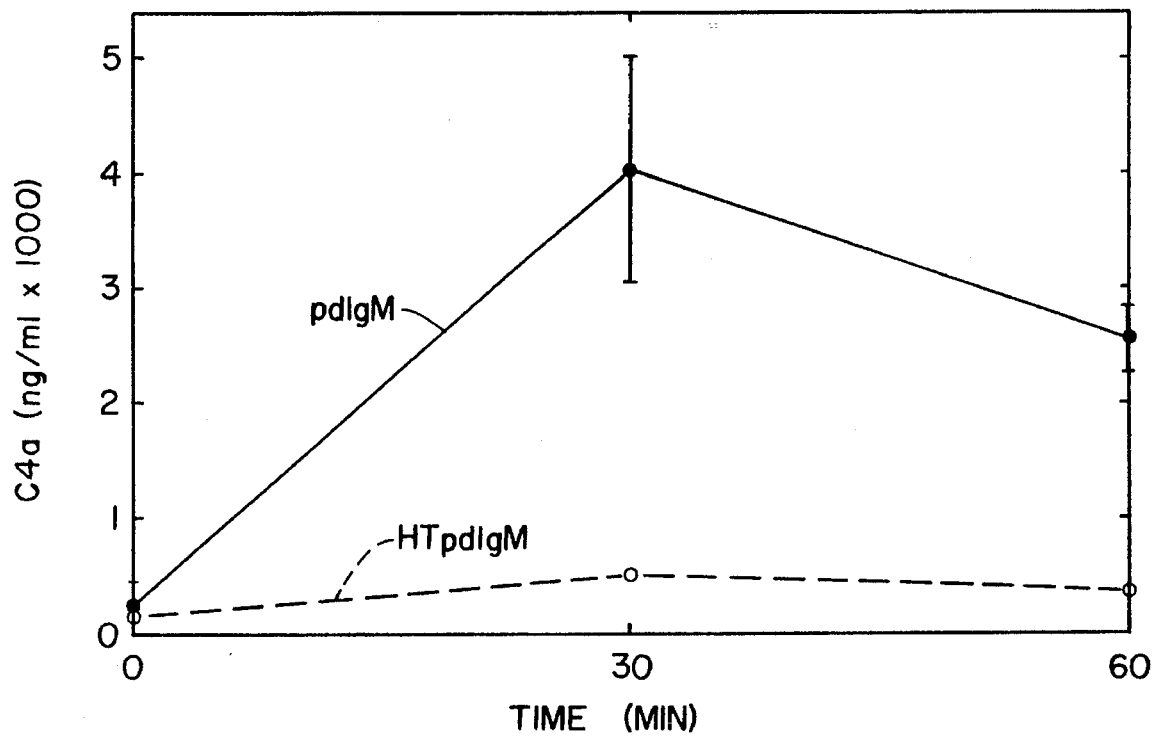
FIG._1.
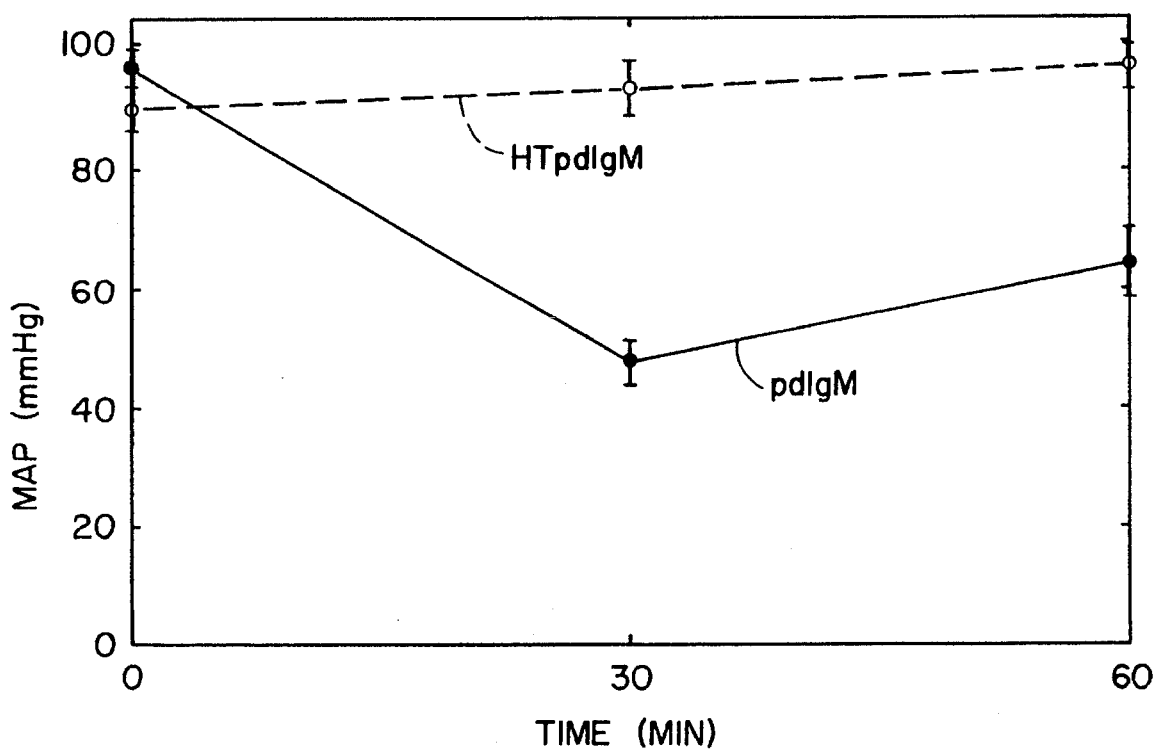
FIG._2.

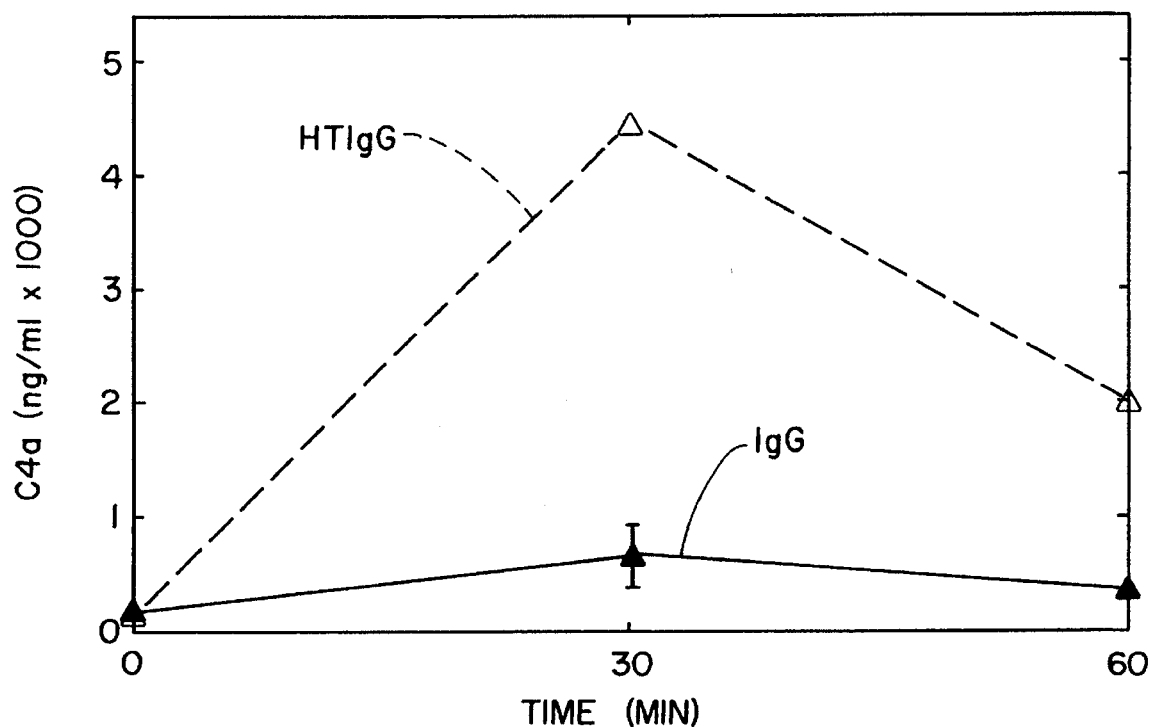
FIG._3.
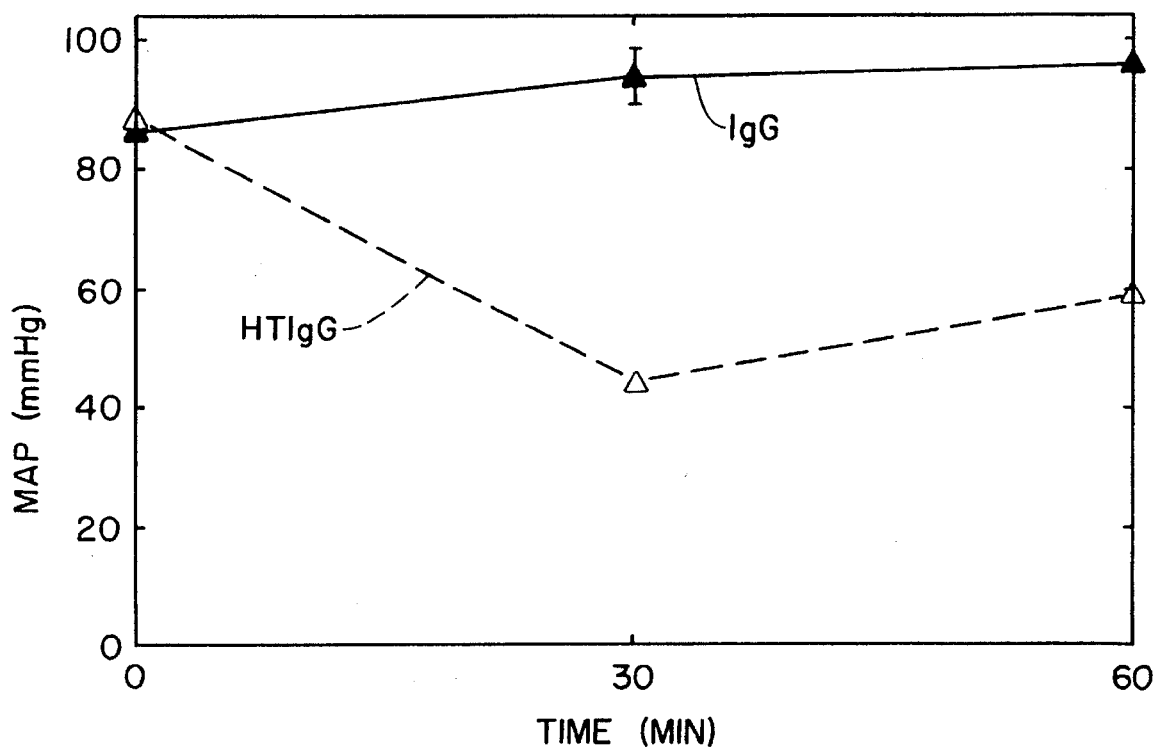
FIG._4.

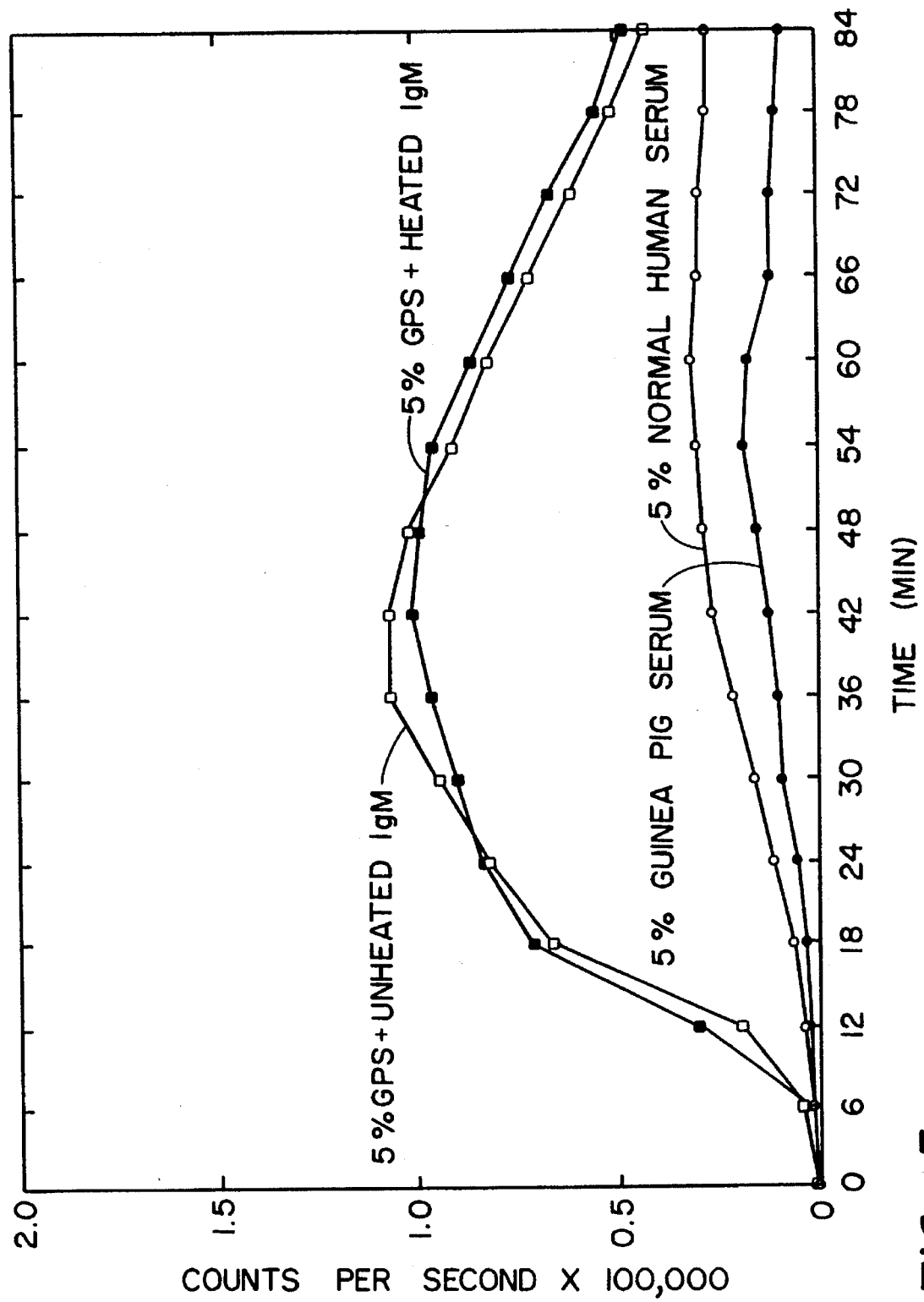
FIG._5.

HEAT-TREATED IGM ANTIBODY PREPARATIONS

This application is a division of application Ser. No. 07/504,161 now U.S. Pat. No. 5,256,771, filed Apr. 3, 1990.

BACKGROUND OF THE INVENTION

1. Field

This disclosure is generally concerned with therapeutic antibody or immunoglobulin preparations and specifically with therapeutic immunoglobulin preparations that include at least some antibodies of the IgM type.

2. Prior Art

Antibodies may be classified according to a well known typing system (i.e. IgM, IgG, IgA, IgD, IgE) and, in case of IgG, according to sub-types (i.e. $IgG_1$, $IgG_2$, $IgG_3$, and $IgG_4$).

Commercially available immunoglobulin preparations (known as immune serum globulin or ISG) commonly consist mainly of antibodies of the IgG type with the distribution of IgG sub-types approximating that found in human plasma. Typically, the amount of IgM in such preparations, if present at all, is relatively small.

IgM is a well known 19S immunoglobulin which comprises about 7% of the immunoglobulins found in man. IgM antibodies are said to have an antibody valence of at least five and they are the earliest antibodies generated in an immune response. Although IgM antibodies tend to be very effective, especially in combating bacterial infections, they have a relatively short in vivo half life of about five days. Further, IgM antibodies tend to aggregate and are relatively difficult to stabilize, especially in purified form.

To date, the only known commercial intravenous (IV) product having significant amounts of IgM antibody is a product known as Pentaglobin™, available from Biotest, GmbH, of West Germany. The use of that product appears to be described in articles by K. D Tympner, et al, "Intravenous IgM-Applikation", Mschr. Kinderheilk. 123, 400–401 (1975) and by K. N. Haque, et al "IgM-Enriched Intravenous Immunoglobulin Therapy in Neonatal Sepsis"Am. J. Dis. Child. 142, 1293–1296 (1988). That product comprises, on a percent by weight total protein basis, about 76% IgG, about 12% IgA and about 12% IgM.

It has been thought that the use of larger amounts of IgM in an ISG product could lead to adverse reactions. For example, it is known that IgM is many times more potent than IgG in activating the complement cascade in an immune reaction. This is because only one molecule of IgM bound to an antigen will activate complement whereas two or more molecules of IgG must be bound to an antigen in close association to each other to activate complement.

It appears that the very production methods used in preparing IgM-enriched products may limit the amount of IgM available due to degradation reactions. See, for example, U.S. Pat. 4,318,902 to W. Stephen, describing the use of β-propriolactone to make an IgM enriched product IV administrable. Hence, for whatever reason, even though IgM is recognized as very effective, it has not appeared in any commercially available intravenously useful ISG product at an amount greater than about 12% by weight total protein. Although a 20% by weight IgM product has been available, in the past (Gamma-M-Konzentrat, Behringwerke AG, Marburg, Germany), it has been made for and limited to intramuscular (not IV) applications.

Various purification schemes have been suggested for plasma-derived IgM and, more recently, monoclonal-derived IgM. In the case of plasma-derived IgM, it has been known since the 1940's that alcohol fractionation techniques could be used to obtain a relatively concentrated IgM from what is known as Cohn Fraction III. See also, for example, the above-cited U.S. Pat. No. 4,318,902 (and the cited references) to W. Stephen concerned with the use of beta-propriolactone to make a concentrated (12%) IgM suitable for intravenous (IV) administration. In addition, see EPO application 0 038 667 of Miura et al (IgM acylation). Other IgM purification or preparation techniques are disclosed by U. Sugg et al, Vox Sang. 36:25–28 (1979); M. Steinbach et al, Preparative Biochemistry 3 (4), 363–373 (1973) and A. Wichman et al, Biochem. Biophys. Acta 490:363–69 (1977). For a variety of technical reasons, plasma derived IgM has been relatively difficult to purify and the highest known purity to date (used in analytical purposes) is about 90% IgM, by weight.

In addition to the above problem associated with IgM-rich preparations, it has been observed that the preparations in use tend to generate what is known as non-specific complement activation. Non-specific complement activation refers to the initiation of the complement cascade even in the absence of antibody-antigen complexing. This phenomenon is often associated with the infusion of aggregates of immunoglobulins. Non-specific complement activation is to be avoided since it may cause undesirable side effects such as hypotension. Specific complement activation, on the other hand, is desirable and it occurs only after the immunoglobulin(s) has bound to, for example, the antigenic surface of a microorganism in the bloodstream.

It has been reported by S. Barandun et al "Intravenous Administration of Human Gamma-Globulin", Vox Sang 7, 157–174 (1962) that human gamma-globulin for intravenous administration heated at 37° C. at pH 3.8–4.0 for 24 hours, followed by pH adjustment to 7.0, resulted in a reduction of anticomplementary activity (AC) measured by complement fixation test. However, this treatment for longer periods of incubation resulted in high anticomplementary activity due to the formation of aggregated gamma-globulin. These authors did not demonstrate retention of specific complement activity by the heated immunoglobulin when bound to antigen. Furthermore, no demonstration of in vivo safety was reported by these authors. In addition, M. Wickerhauser et al "Large Scale Preparation of Macroglobulin" Vox Sang 23, 119–125 (1972) demonstrated that IgM concentrates prepared by PEG precipitation had high anticomplementary activity (AC) by standard complement fixation test and this AC activity was reduced 10 fold by incubating the IgM concentrate at pH 4.0 at 37° C. for 8 hours followed by readjustment to neutral pH. Similar to the previous paper (Vox sang 7, 157–174 (1962), these authors did not assess the specific complement activating potential of the heated IgM concentrate, nor did they assess safety in any animal model.

We have now found that the problem of non-specific complement activation associated with IgM or IgM rich immunoglobulin preparations can be minimized (without losing specific complement activation) in a relatively simple and surprising way.

SUMMARY OF THE INVENTION

Our method of substantially eliminating non-specific complement activation in an IgM-containing immunoglobulin preparation while retaining specific complement activation effector functions comprises the step of subjecting the preparation to a gentle heating step under conditions sufficient to eliminate the non-specific complement activation while not adversely affecting the normal biological activity or antigen binding ability of the IgM antibody. To do this, we have found that the heating step should be at a temperature ranging from about 40° C. to 62° C., preferably about 45° to 55° C. for at least about 10 min. and the preparation should be in an aqueous solution having an acid pH ranging preferably from about 4.0 to 5.0. To date, the preferred temperature appears to be at or very close to 50° C. for at least about 30 minutes.

Our improved product comprises an immunoglobulin preparation which includes at least some measurable antibodies of the IgM type. On a dry weight basis, a preferred product comprises at least 20% antibodies of the IgM type, the remainder of the antibodies being mainly of the IgG type. Trace amounts (less than 20% by weight) of other types may be present. Details of our preferred product and processes are given below.

BRIEF DESCRIPTION OF THE FIGURES

FIG. 1 represents plasma $C4_a$ anaphylatoxin levels in monkeys infused with plasma derived IgM (pdIgM) or heat-treated plasma derived IgM (HT pdIgM).

FIG. 2 represents mean arterial blood pressure (MAP) measurements in monkeys infused with plasma derived IgM (pdIgM).

FIG. 3 represents plasma $C4_a$ anaphylatoxin levels in monkeys infused with native intravenous gamma globulin (IgG) or heat-treated intravenous gamma globulin at neutral pH (HTIgG).

FIG. 4 represents mean arterial blood pressure (MAP) measurements in monkeys infused with native intravenous gamma globulin (IgG) or heat-treated intravenous gamma globulin at neutral pH (HTIgG).

FIG. 5 represents ability of unheated or heated IgM to promote phagocyte chemiluminescence against E. Coli 0.50:kl bacteria.

SPECIFIC EMBODIMENTS

Work in our laboratory has demonstrated a reproducible adverse response elicited by infusion of IgM-enriched, IgG immunoglobulin concentrates in the pentobarbital-anesthetized cynomolgus monkey. That product consisted of about 50% by weight IgM on a dry weight basis, the remaining being IgG. The mixture was given IV as a 5% aqueous solution. The rate of administration was 1 mg/kg/min (IgM) to a total dose of 50 mg/kg. A major component of the adverse response was a severe decline in arterial blood pressure. In attempting to understand the mechanism of the adverse effect, we demonstrated that heat-aggregated IgG prepared at neutral pH (not acid pH) when infused in the monkey elicited effects remarkably similar to those observed following the infusion of IgM-enriched, IgG immunoglobulin concentrates. Since both the IgM-enriched, IgG immunoglobulin concentrates and aggregates of IgG formed at neutral pH are capable of activating the classical pathway of complement, we hypothesized that complement activation is associated with elicitation of the adverse effect in the cynomolgus monkey. The classical complement pathway is described in Inflammation: Basic Principles and Clinical Correlates Complement: Chemistry and Pathways, pp 21–53. the teachings of which are incorporated herein by reference (Raven Press, New York N.Y., 1988).

The complement system functions primarily as an effector mechanism in the immune defense against microbial infection. The activated products of the complement system, attract phagocytic cells and greatly facilitate the uptake and destruction of foreign particles by opsonization. There are two pathways for activating complement, the classical pathway and the alternate pathway. Activation of the classical pathway is initiated by antigen-antibody complexes or by antibody bound to cellular or particulate antigens. The alternate pathway is activated independent of antibody by substance such as bacterial wall constituents, bacterial lipopolysaccharides (LPS), cell wall constituents of yeast (zymosan) and Fungi. It is thought that the alternate pathway provides protection against infection prior to an immune response whereas the classical pathway is important after antibody production has occurred.

Activation of the blood complement system generates bioactive peptide fragments called anaphylatoxins. Complement 4a (C4a) anaphylatoxin is a split product of C4 (MW 8740). When C1q is activated by antigen-antibody complexes or aggregates, the C1 complex splits C4 into C4a and C4b allowing C4b to bind to the activating surface while C4a anaphylatoxin is released into plasma. Recent developments in analytical biochemistry have provided techniques which permit the measurement of plasma C4a by radioimmunoassay. See, for example, U.S. Pat. 4,731,336 and European Pat. 97,440 both to P. S. Satoh.

Determination of C4a levels in plasma provides direct information regarding activation of the classical complement cascade in vivo. Furthermore, the induction of C4a generation in vitro, by various immunoglobulin preparations using human serum as the complement source, is correlated with in vivo complement activation in the monkey following infusion of the immunoglobulins.

In the studies described herein, we determined whether adverse effects (hypotension) elicited by IgM-enriched, IgG immunoglobulin concentrates and/or heat-aggregated IgG formed at neutral pH are associated with elevated levels of plasma C4a. In addition, non-specific activation of complement (classical pathway) induced by the immunoglobulin preparations was assessed by C4a generation in vitro.

Using these assay systems, we, furthermore, demonstrate that mild heat-treatment of IgM-enriched, IgG immunoglobulin concentrates diminishes C4a generation in vitro and correspondingly this mild heat-treatment diminishes adverse side effects (hypotension) associated with parenteral (IV) administration in the non-human primate. Finally, we demonstrate that the mild heat-treatment process step did not significantly effect the antigenic determinants of either IgM or IgG or the specific antigen binding sites; thus the effector functions of the immunoglobulin are unaltered. Retention of the desired specific complement activation properties of the immunoglobulin was confirmed in subsequent opsonic studies.

Methods

Adverse effects (hypotension) induced by the various immunoglobulin preparations were assessed in the cynomolgus monkey. The monkeys were anesthetized by an intramuscular injection of Ketamine hydrochloride (5 mg/kg). Following intubation, anesthesia was maintained by intravenous pentobarbital sodium (5–10 mg/kg as needed). Catheters were inserted in the femoral artery and vein for measurement of mean arterial blood pressure and parenteral administration of the immunoglobulin preparations, respectively.

For the IgM enriched, IgG immunoglobulin concentrates we used an infusion rate of 1 mg/kg/min (IgM) up to a total dose of 50 mg/kg. This rate and dose resulted in severe hypotension within 30 minutes (data to be presented).

Blood pressure measurements were taken from the femoral artery over a 90 minute time period since we have demonstrated that adverse effects, if they result, will occur within this time frame. C4a anaphylatoxin measurements were performed on plasma from whole blood (anticoagulated with Citrate) obtained at 0, 30, 60 and 90 minutes. The samples were stored at −70° C. C4a measurements were made by radioimmunoassay with kits from Amersham International (Arlington Heights, Ill.).

Definitions

As used herein, the expression antibody (or immunoglobulin) preparation means a collection of therapeutic antibodies comprising at least about 20% by weight of antibodies of the IgM type, the remaining antibodies, if present, being mainly antibodies of the IgG type with trace amounts other types such as IgA, etc. The individual antibodies can be obtained from a variety of sources such as plasma (as described above, for example) or from cell culture systems (e.g. monoclonal antibodies from hybridomas or transformed cell lines). In the examples below, our enriched IgM antibody preparation comprised on average about 30% to 50% by weight antibodies of the IgM type, the remaining antibodies being mainly of the IgG type.

Non-specific complement activation means the activation of the complement cascade by immunoglobulin in the absence of antigen.

Minimal non-specific complement activation means the generation of less than about 1.0 ug/ml $C4_a$ in an in vitro assay in the absence of antigen. Alternatively, minimal non-specific complement activation means an amount of $C4_a$ generation within about 100% of the amount of $C4_a$ generated using a liquid IVIG at pH 4.25 as a control.

Specific complement activation means the activation of the complement cascade by immunoglobulin (of the IgM or IgG type) in the presence of antigen.

Substantially no loss of specific complement activation, as applied to an IgM enriched antibody preparation, means the antibody preparation is capable of binding to antigen and activating the classical pathway of complement in vitro or in vivo.

Materials

Pd IgM Immunoglobulin Concentrate Preparation

Pd IgM immunoglobulin concentrates were isolated from Cohn fraction III paste (45 kg) suspended in 12.5 volumes of 0.05M acetate buffer pH 3.5–4.0 and mixed at room temperature for 2–3 hours. To the mixture was added 2.0% of caprylic acid by vol/wt at pH 4.8 to remove lipoproteins and prekallikrein activator (PKA) by centrifugation. The extracted caprylate supernatant, after diafiltration and ultrafiltration through PM-30, resulted in low conductivity of 0.03 –0.06 mm ho/cm at pH 4.8 . Virus inactivation was achieved with 0.3% TNBP/1% Tween-80 at 24° C. for more than 6 hours. The caprylate supernatant was precipitated with buffer system such as tris (0.0101 vol. of I M Tris pH 7.8) or imidazole buffer (0.005 vol. of 1M imidazole pH 7.8) sterile water, adjusting pH to 4.0 –4.8 with acetic acid, and further diafiltered/ultrafiltered against water, then adding solid glycine to a final concentration of 0.25M glycine, pH 4.0–4.8. The Pd IgM immunoglobulin concentrates resulted in low PKA (less than 10% of reference) and less than 5% aggregate determined by high pressure liquid chromatography (HPLC), The final IgM-enriched product consisted of 50–60% IgM, 30–40% IgG, 3–5% IgA, on a dry weight basis, in a total 5% protein aqueous solution.

Heat-Aggregated IgG Preparation

A 5% solution of IGIV (Lot #2855–11B) was used as an appropriate antibody control. A heat-aggregated IgG solution was prepared from the 5% IGIV solution by heating at 62° C. for 1 hour (pH 7.0). Another heat-aggregated IgG solution was prepared from the 5% IGIV solution by heating at 62° C. for 2 hour (pH 4.25).

Heat Treated IgM, IgG Preparation

The heat-treatment of the IgM, IgG preparation in water or glycine (pH 4.0–4.8) ranged from 37° C. to 62° C. for periods of 10 minutes to 8 hours to determine the optimal mode for the treatment.

Assay Methods

Aggregate Determination by High Pressure Liquid Chromatography (HPLC)

Aggregate formation in the native IgM and IgG preparations or induced by heating was determined by high pressure liquid chromatography with TSKG 4000 SWXL gel (7.8× 300 mm, 8 μm particle size, Toyo Soda Corporation, Japan) and eluted with 0.05M sodium acetate, 0.20M sodium sulfate, pH 5.0.

Biological and Functional Activity Determination of Immunoglobulin Concentrates

1. Antigenic Determinants of IgM-enriched, IgG by Radial Immunodiffusion (RID)

The concentration and antigenic determinants of IgM and IgG were determined by radial immunodiffusion (RID) with quiplate system from Helene Laboratories (Beaumont, TX). This method provides an indirect assessment of the integrity of the antibody.

2. Specific Antigen Binding Sites Study by ELISA against Ps. IT$_4$LPS

The biological activity of IgM immunoglobulin concentrates and mild heat treated IgM concentrates was determined by enzyme-linked immunosorbent assay (ELISA) to quantitate IgM binding to Ps. IT$_4$LPS (lipopolysaccharide) and to assess the integrity of specific antigen binding sites. 10 μg of P. aeruginosa immunotype 4 LPS in 0.06M sodium carbonate buffer pH 9.5 were coated to Immulon 1 plates (Dynatech Lab) at 37° C. for 3 hours. Each well of the plates was washed twice with PBS - 0.05% Tween buffer. The standard Pseudomonas monoclonal antibody and unheat/ heat treated IgM concentrates were diluted in 0.01M Tris buffer pH 7.8 containing BSA and added to the plates incubated at room temperature overnight. Each well was washed three times with PBS - Tween buffer. Goat anti-human IgM alkaline phosphatase conjugate (HyClone, Logan, Utah) was added to the wells, incubated at room temperature for 4 hours and the wells were washed five times with PBS - Tween buffer. P-Nitrophenyl phosphate in diethanolamine pH 9.8 substrate solution was added to each well at room temperature for 30 minutes and the A405 nm/450 nm was read.

3. Specific Complement Activity Determination by Phaqocytic Assay

A phagocytic assay was employed to determine the opsonic activity (specific complement activity) of mild heat treated IgM immunoglobulin concentrates. The phagocytic assay employed bacteria (E. coli 050:k1) and human phagocytes (PMNs) suspended in tissue culture fluid. The bacteria to PMN ratio was 20 to 1 and 5% (vol/vol) guinea pig serum (GPS) served as complement source. 2.5 ul of IgM concentrates was added to the total assay mixture (500 ul) and incubated at 37° C. for 100 minutes. An aliquot of the assay mixture was added to 9 vol. of distilled water to lyse PMNs and surviving bacteria were enumerated by duplicate agar plate counts.

4. In vitro and in vivo Non-specific Complement Activation assessed by Anaphylatoxin $C4_a$ Generation The ability of various immunoglobulin preparations to activate the classical pathway of complement in vitro was assessed by incubation of the respective preparations (1.47 mg IgM or IgG/ml serum) with human serum at 37° C. for 20 minutes and determining the resultant generation of $C4_a$ levels by radioimmunoassay (RIA). The RIA kits were obtained from Amersham (Arlington Heights, Ill.).

Systemic complement activation in vivo was assessed by measuring plasma $C4_a$ levels following parenteral administration of the various immunoglobulin preparations in the monkey. Antibodies raised against human $C4_a$ (RIA kits) partially cross react with monkey $C4_a$, approximately 60%.

Results

Table 1 describes the immunoglobulin preparations used in the initial experiments designed to examine the hypothesis that non-specific complement activation may be associated with adverse cardiovascular events following intravenous infusion. To test this hypothesis various immunoglobulin preparations were assayed for their ability to activate the classical pathway of complement in vitro by measuring $C4_a$ generation employing human serum as the complement source. Mean arterial blood pressure in the cynomolgus monkey was measured over a 90 minute period following infusion of the immunoglobulins in order to assess cardiovascular safety. Plasma $C4_a$ levels were also measured in order to ascertain complement activation following infusion.

In Vitro Data

A 5% IGIV immunoglobulin (control) solution at 0.2M glycine pH 4.25 did not cause appreciable $C4_a$ generation in vitro when incubated with human serum (<1%, 0.23 ug/ml). The enriched pd IgM, prepared by euglobulin precipitation in a similar glycine buffer pH 4.25, caused substantial $C4_a$ generation in vitro (4.5 ug/ml). To prepare aggregated IgG, a well known activator of complement, we heated the 5% IGIV protein solution at pH 7.0 at 62° C. for 1 hour. This heat treatment resulted in a solution which had 19% pentamer aggregates yet retained over 72% of its antigenic determinants as assessed by RID. This immunoglobulin solution also generated a substantial amount of $C4_a$ (14.0 µg/ml) when incubated with human serum. However, the same IGIV solution when heated at pH 4.25, although generating 58% aggregates (size less than pentamer), did not generate significant amounts of $C4_a$ in vitro (0.56 ug/ml). This IGG Solution also lost over 80% of its antigenic determinants as measured by RID.

TABLE 1

Characteristics of Immunoglobulin Preparations

| Antibody | Lot # | Buffer | Heat (hrs) 62° C. | RID IgM mg/ml | RID IgG mg/ml | % Aggregates <Pentamer | % Aggregates >Pentamer | $C_{4a}$ Generated in vitro (Human) Serum) (ug/ml) |
|---|---|---|---|---|---|---|---|---|
| IGIV (5%) | 2855-11-B | 0.2M Glycine pH 4.25 | 0 | 0 | 57.0 | 0 | 0 | 0.23 |
| pdIgM | 3747-82-E | 0.2M Glycine pH 4.25 | 0 | 36.0 | 26.2 | 0 | 6.0 | 4.5 |
| IGIV (HT) | 18053-79-8 | 0.2M Glycine pH 7.0 | 1 | 0 | 40.9 | 11.0 | 19.0 | 14.0 |
| IGIV (HT) | 18053-66-2 | 0.2M Glycine pH 4.25 | 2 | 0 | 10.2 | 58.0 | 0 | 0.56 |

These results demonstrate that both pdIgM, IgG immunoglobulin concentrates and heat-aggregated IGIV at pH 7.0 induced substantial $C4_a$ generation in vitro while native IGIV and heated IGIV at pH 4.25 generated non-significant quantities of $C4_a$ anaphylatoxin.

It was important to determine whether these in vitro measurements of non specific complement activation were associated with adverse cardiovascular effects in the cynomolgus monkey when the immunoglobulin solutions were intravenously infused.

TABLE 2

Acute Effect of Immunoglobulin Preparations on MAP and Plasma $C4_a$ Anaphylatoxin Levels in the Monkey

| Antibody | Rate | Dose | Time (min.) 0 | 30 | 60 | 90 |
|---|---|---|---|---|---|---|
| IGIV (5%) N = 3 | 10 mg/Kg/min | 500 mg/Kg MAP (mm Hg) | 85 ± 5 | 97 ± 4 | 96 ± 7 | 97 ± 6 |
| | | $C4_a$ (ng/ml) | 192 ± 91 | 601 ± 95 | 385 ± 51 | 392 ± 180 |
| pdIgM N = 5 | 1 mg/Kg/min | 50 mg/Kg MAP (mm Hg) | 97 ± 4 | 47 ± 3 | 67 ± 6 | 64 ± 10 |
| | | $C4_a$ (ng/ml) | 253 ± 43 | 4048 ± 1000 | 2562 ± 370 | 611 ± 305 |
| IGIV (5%) pH 7.0 Heated N = 3 | 1 mg/Kg/min | 20 mg/Kg MAP (mm Hg) | 99 ± 5 | 47 ± 6 | 57 ± 7 | 63 ± 7 |
| | | $C4_a$ (ng/ml) | 135 ± 38 | 4160 ± 268 | 3100 536 | 1558 ± 131 |

TABLE 2-continued

Acute Effect of Immunoglobulin Preparations on MAP and
Plasma $C4_a$ Anaphylatoxin Levels in the Monkey

| Antibody | Rate | Dose | Time (min.) | | | |
|---|---|---|---|---|---|---|
| | | | 0 | 30 | 60 | 90 |
| IGIV (5%) pH 4.25 Heated N = 3 | 10 mg/Kg/min | 500 mg/Kg MAP (mm Hg) $C4_a$ (ng/ml) | 87 ± 3  155 ± 17 | 85 ± 14  535 ± 51 | 97 ± 7  372 ± 100 | 99 ± 6  207 ± 30 |

Table 2 and FIGS. 1–4 presents the in vivo results with these respective immunoglobulin preparations. These results demonstrate that the immunoglobulin preparations which generated substantial $C4_a$ levels in vitro i.e., pdIgM and heat-aggregated IGIV at pH 7.0, caused severe hypotension in the cynomolgus monkey and elevated plasma $C4_a$ levels, while those immunoglobulin preparations which did not generate substantial $C4_a$ in vitro i.e., native IGIV and heat aggregated IGIV at pH 4.25, did not cause hypotension in the cynomolgus monkey and did not greatly increase plasma $C4_a$ levels. Thus, the in vitro assessment of $C4_a$ generation by the various immunoglobulin preparations appeared to be associated with adverse cardiovascular effects in vivo following intravenous infusion.

Since an IGIV protein solution heated at pH 4.25 did not cause substantial $C4_a$ generation in vitro and did not cause hypotension when infused intravenously, we reasoned that perhaps heating the pdIgM, IgG immunoglobulin concentrate at pH 4.25 would diminish the non-specific complement activating potential of the IgM, without adversely affecting the IgG which is present in the solution. That is, heating IgG at acidic pH did not result in a solution which activated complement in vitro and did not have adverse effects when infused in the cynomolgus monkey. To test this hypothesis we initially heated the pdIgM, IgG immunoglobulin solution at 62° C. for 2 hours and evaluated its $C4_a$ generating potential in vitro. This solution did not generate significant amounts of $C4_a$ in vitro (0.27 ug/ml) and did not cause hypotension or substantial increases in plasma $C4_a$ when infused in the cynomolgus monkey, Table 3a, 3b and FIGS. 1, 2.

TABLE 3a

Characteristics of Heat
Treated PdIgM, IgG Immunoglobulin Concentrate

| Antibody | RID | | % Aggregates >Pentamer | $C4_a$ Generated in vitro (Human Serum) ug/ml |
|---|---|---|---|---|
| | IgM mg/ml | IgG mg/ml | | |

TABLE 3a-continued

| pd IgM (pH 4.25) (HT 62° C., 2 hrs) | 6.58 | 12.81 | 47.0 | 0.27 |

TABLE 3b

Acute Effect of Heat Treated PdIgM, IgG Immunoglobulin
Concentrate on MAP and Plasma $C4_a$ Anaphylatoxin Levels
in the Monkey (N = 3)

| Antibody | Rate | Dose | Time (min.) | | | |
|---|---|---|---|---|---|---|
| | | | 0 | 30 | 60 | 90 |
| PdIgM (pH 4.25) (HT 62° C. 2 hrs) | 2 mg/kg/min | 100 mg/kg MAP (mm Hg) $C4_a$ (ng/ml) | 90 ± 3  155 ± 19 | 94 ± 4  530 ± 25 | 98 ± 4  372 ± 75 | 97 ± 5  251 ± 60 |

These results demonstrate that heating (62° C. for 2 hours) an IgM, IgG immunoglobulin concentrate at acid pH (4.25) produces a protein solution which has dramatically diminished non-specific complement activating potential in vitro and does not cause hypotension when infused in the cynomolgus monkey. However, this particular heat treatment (62° C. for 2 hrs) resulted in a loss of more than 80% of the IgM antigenic determinants and a greater than 47% pentameric aggregate formation, Table 3.

Thus, although, this heat-treatment diminished the adverse cardiovascular effects associated with intravenous administration, it also appeared to diminish the effector functions of the immunoglobulin. We, therefore, sought to define more closely an optimal heating temperature and incubation time which would result in an IgM, IgG immunoglobulin concentrate which had minimal non-specific complement activating potential while retaining relevant biologic effector functions, i.e., antigen binding, opsonization, etc.

During this evaluation, a number of conditions were examined. Table 4 summarizes data concerning the effect of temperature and incubation time on $C4_a$ anaphylatoxin generation in vitro.

TABLE 4

Effects of Temperature and Incubation Time on $C_{4a}$*
Generation in vitro and IgM Antigenic Determinants of IgM,
IgG Immunoglobulin Concentrates (3747-82-E, pH 4.42)

| Incubation Time (Min) | 62° C. $C_{4a}$ µg/ml | 62° C. IgM mg/ml | 55° C. $C_{4a}$ µg/ml | 55° C. IgM mg/ml | 52° C. $C_{4a}$ µg/ml | 52° C. IgM mg/ml | 50° C. $C_{4a}$ µg/ml | 50° C. IgM mg/ml | 45° C. $C_{4a}$ µg/ml | 45° C. IgM mg/ml | 40° C. $C_{4a}$ µg/ml | 40° C. IgM mg/ml |
|---|---|---|---|---|---|---|---|---|---|---|---|---|
| 0 | 10.41 | 35.82 | 10.41 | 35.82 | 10.41 | 35.82 | 10.41 | 35.82 | 10.41 | 35.82 | 10.41 | 35.82 |
| 10 | 0.49 | 17.42 | 1.08 | 33.49 | 2.43 | 35.14 | | | | | | |
| 20 | 0.49 | 14.58 | 0.51 | 31.21 | 1.85 | 35.14 | 5.41 | 35.82 | | | | |
| 30 | 0.62 | 10.68 | 0.35 | 26.77 | 1.45 | 35.14 | | | | | | |
| 40 | | | 0.60 | 26.77 | 1.24 | 35.14 | 2.88 | 35.82 | | | | |
| 60 | 0.07 | 4.9 | 0.48 | 22.50 | 1.09 | 35.39 | 2.12 | 33.49 | 5.08 | 35.68 | 12.25 | 35.68 |
| 120 | | | 0.50 | 12.54 | 0.60 | 35.00 | 1.49 | 33.49 | 4.35 | 35.68 | 7.41 | 35.68 |
| 180 | | | | | 0.82 | 33.41 | 0.77 | 32.28 | 3.25 | 35.68 | 5.24 | 35.68 |
| 240 | | | | | | | 0.67 | 24.40 | 2.74 | 35.68 | 5.24 | 35.68 |
| 300 | | | | | | | 0.86 | 24.40 | 3.86 | 35.68 | 5.60 | 35.68 |
| 480 | | | | | | | | | 4.13 | 35.68 | 5.26 | 35.68 |

*Control (no exogenous immunoglobulins) $C_{4a}$ levels have been subtracted from all reported values.

PdIgM, IgG immunoglobulin concentrates (50% IgM, pH 4.24) heated at 62° C. for 10 minutes caused non-significant $C_{4a}$ generation in vitro (0.49 ug/ml) but approximately 50% of IgM antigenic determinants were lost. Heating the IgM, IgG immunoglobulin concentrate at 55° C. for 30 minutes decreased $C_{4a}$ generation to 0.35 ug/ml in vitro and the IgM immunoglobulin retained more than 75% of its antigenic determinants. Heating at 52° C. for 120 minutes decreased $C_{4a}$ generation to 0.60 ug/ml and immunoglobulin retained more than 98% of its antigenic determinants. Heating at 50° C. for 180 minutes decreased $C_{4a}$ generation to 0.77 ug/ml and the immunoglobulin retained more than 92% of its antigenic determinants. Immunoglobulin heated at 45° C.–37° C. retained substantial $C_{4a}$ generating potential (>4 ug/ml) and did not demonstrate any decrease in IgM antigenic determinants.

We next examined the effects of pH, IgM concentration and incubation times on $C_{4a}$ generation in vitro, Table 5. Temperature was held constant at 50° C.

TABLE 5

Effects of pH, IgM Concentration and Incubation Time on $C_{4a}$
Generation* in vitro and IgM Antigenic Determinants of IgM
Immunoglobulin Concentrates at 50° C.

| Incubation Time (Min) | 50% IgM pH 4.42 $C_{4a}$ µg/ml | 50% IgM pH 4.42 IgM mg/ml | 50% IgM pH 4.24 $C_{4a}$ µg/ml | 50% IgM pH 4.24 IgM mg/ml | 20% IgM pH 4.25 $C_{4a}$ µg/ml | 20% IgM pH 4.25 IgM mg/ml |
|---|---|---|---|---|---|---|
| 0 | 7.06 | 37.90 | 5.45 | 37.90 | 5.00 | 10.07 |
| 15 | 2.76 | 37.90 | 1.22 | 37.90 | 1.26 | 10.07 |
| 30 | 2.52 | 37.90 | 0.98 | 35.56 | 0.88 | 10.38 |
| 45 | 2.12 | 37.90 | 1.03 | 35.56 | 0.96 | 10.38 |
| 60 | 2.08 | 36.73 | 0.54 | 33.27 | 0.94 | 9.77 |
| 90 | 1.74 | 37.90 | 0.98 | 33.27 | | |
| 120 | 1.20 | 35.56 | 0.79 | 28.81 | 0.94 | 8.32 |
| 150 | 1.03 | 36.73 | | | | |
| 180 | 0.88 | 37.90 | 0.56 | 26.65 | 0.90 | 6.1 |

*Control (no exogenous immunoglobulins) $C_{4a}$ levels have been subtracted from all reported values.

Pd IgM immunoglobulin concentrates containing 50% IgM at pH 4.42 heated at 50° C. for 3 hours resulted in a decrease in $C_{4a}$ generation from 7.06 µg/ml to 0.88 µg/ml and fully retained IgM antigenic determinants. Pd IgM immunoglobulin concentrates containing 50% IgM at pH 4.24 heated at 50° C. for 60 minutes caused $C_{4a}$ generation in vitro to decrease to 0.54 µg/ml and still retained significant IgM antigenic determinant (88%). IgM concentrates containing 20% IgM at pH 4.25 heated at 50° C. for 30 minutes caused $C_{4a}$ generation to decrease to 0.88 µg/ml with little loss of IgM antigenic determinants and further incubation for 180 minutes did not cause any additional decrease in $C_{4a}$ generation in vitro but resulted in a loss of IgM antigenic determinants (40%).

In order to further evaluate the effects of heating on immunoglobulin effector functions we assayed antigen binding activity of IgM to ps. $IT_4$ lipopolysaccharide under various heating conditions. These results are summarized in Table 6.

TABLE 6

Effects of Temperature and Incubation Time on Antigenic
Determinants and Specific Antigen Binding Activity of Pd
IgM Concentrates.

| Sample | Heat °C. | Heat Min. | RID IgM mg/ml | ELISA α Ps $IT_4$ LPS mg/ml | Specific Activity α LPS mg/mg IgM |
|---|---|---|---|---|---|
| 3747-82-E (pH 4.42) | — | — | 36.0 | 0.542 | 0.015 |
| 18107-58-1 | 62 | 10 | 17.42 | 0.400 | 0.023 |
| 18053-62-6 | 62 | 120 | 6.58 | 0.040 | 0.006 |
| 18107-62-3 | 55 | 30 | 26.77 | 0.518 | 0.019 |
| 18107-62-5 | 55 | 50 | 24.61 | 0.364 | 0.015 |
| 18107-72-9 | 52 | 150 | 35.00 | 0.483 | 0.014 |
| 18107-72-11 | 52 | 210 | 32.32 | 0.455 | 0.014 |
| 18107-63-7 | 50 | 180 | 32.38 | 0.427 | 0.013 |
| 18107-67-15 | 45 | 480 | 35.68 | 0.604 | 0.017 |
| 18107-70-1 | 50 | 180 | 32.90 | 0.419 | 0.013 |

Pd IgM, IgG concentrates heated at 62° C. for 120 minutes adversely affected the IgM antigenic determinants, resulting in a loss of more than 90% of specific antigen binding activity, and also a 3 fold reduction in specific activity (e LPS/IgM). Samples treated at the lower temperatures all retained significant specific antigen binding activity and non-significant decrease in specific activity.

We next examined what effect heating had on opsonic activity, another important indicator of biologic effector function. These results are summarized in Table 7.

TABLE 7

Effect of Temperature and Incubation Time on Opsonic Activity of a 50% IgM concentrate

| Incubation Time (min.) | $LOG_{10}$ CFU Reduction of *E. Coli* 050:K1 °C. | | | | | |
|---|---|---|---|---|---|---|
| | 62 | 55 | 50 | 45 | 40 | 37 |
| 0 | 3.12 | 2.86 | 2.86 | 2.86 | 2.86 | 2.86 |
| 10 | 0.25 | 2.81 | | | | |
| 20 | 0.19 | 1.79 | 3.23 | | | |
| 40 | | 0.55 | 3.35 | | | |
| 60 | 0.17 | 0.42 | 3.27 | | | |
| 120 | | 0.51 | 3.07 | | | |
| 180 | | | 2.71 | | | |
| 240 | | | 2.19 | | | |
| 300 | | | 2.18 | | | |
| 480 | | | | 3.09 | 3.21 | 3.09 |
| 5% Guinea Pig Serum Only | 0.15 | 0.41 | 0.41 | 0.41 | 0.41 | 0.41 |

Unheated IgM significantly enhanced bacterial killing. IgM, IgG concentrates heated at 62° C. for 10 minutes lost substantial opsonic activity. Concentrates heated at 55° C. had diminished activity at 20 minutes and lost substantial opsonic activity at 40 minutes. Heating at 50° C. slightly reduced opsonic activity over time but substantial opsonic activity still remained at 5 hours. Heating at temperature between 45° C.–37° C. did not diminish opsonic activity over 8 hours.

Opsonic activity of the IgM, IgG immunoglobulin concentrate heated at 50° C. for 3 hours was also assessed in a phagocyte chemiluminescence assay against *E. coli* 050:K1, FIG. 5. Heating IgM at 50° C. for 3 hours leaves intact the ability of IgM to promote chemiluminescence and phagocytic killing of the bacteria.

Since IgM, IgG immunoglobulin concentrates heated at 50° C. for 3 hours retained effector functions i.e., opsonophagocytic activity, antigenic binding sites, etc., and demonstrated diminished non-specific complement activation in vitro ($C4_a$ generation), we assessed the cardiovascular effects of this preparation following intravenous infusion in the cynomolgus monkey. This data is summarized in Table 8.

TABLE 8

Acute effect of heat treated IgM, IgG immunoglobulin concentrates on MAP and plasma $C4_a$ anaphylatoxin levels in the monkey (N = 3).

| | Time (min.) | | | |
|---|---|---|---|---|
| | 0 | 30 | 60 | 90 |
| MAP (mmHg) | 92 ± 7 | 85 ± 5 | 88 ± 9 | 93 ± 7 |
| $C4_a$ (ng/ml) | 85 ± 17 | 326 ± 102 | 500 ± 52 | 685 ± 61 |

IgM, IgG heated at 50°–51° C. for 3 hours.
Rate 1 mg/kg/min
Dose 50 mg/kg

Severe hypotension was not observed in these monkeys following infusion of the immunoglobulin concentrates and plasma $C4_a$ levels were much diminished compared with animals infused with the unheated IgM preparation (Table 2).

Discussion

The parenteral administration of IgM enriched IgG (IgM, IgG immunoglobulin concentrates) is associated with serious side effects including severe systemic hypotension in the cynomolgus monkey. The mechanism whereby IgM, IgG concentrate infusion elicits these adverse effects is not presently known.

In these experiments, however, we have shown that the ability of various immunoglobulin preparations to induce systemic hypotension is related to their capacity to activate the classical complement pathway. That is, immunoglobulin preparations which activate the classical pathway of complement in vitro, (i.e., pdIgM and heat-treated IgG at neutral pH) elicit systemic hypotension when administered intravenously to the monkey. While immunoglobulin preparations which do not activate the classical pathway of complement in vitro, (e.g., heat-treated pdIgM, native IgG and heat-treated IgG at acid pH) do not elicit any adverse hemodynamic effects when administered intravenously to the monkey.

It therefore appears that the invitro assessment of complement activation (classical pathway) of various immunoglobulin preparations has predictive value for estimating the capability of these preparations to elicit adverse effects in the monkey. Whether this is a direct cause and effect relationship or these phenomenon are merely temporarily related has not been determined. Furthermore, and of greater importance, we have shown that mild heat-treatment of pdIgM, IgG immunoglobulin concentrates diminishes its potential to non-specifically activate complement in vitro and this terminal process treatment greatly decreases it's ability to induce adverse cardiovascular effects (hypotension) in our mammal model, the cynomolgus monkey.

Since antigenic determinants and specific antigen binding sites are retained with less harsh heat-treatment (at the presently preferred temperature of about 50° C. for 3 hours) it would appear that antibody integrity has not been compromised at these temperatures while non-specific complement activating potential has been dramatically diminished, thus this treatment would result in a much better product.

It has now been demonstrated that IgM-enriched, IgG immunoglobulin concentrates can be heat treated at elevated temperatures for extended periods of time without significant loss of antigenic determinants or specific antigen binding sites. The preparations still retain opsonophagocytic activity while exhibiting dramatically diminished non-specific complement activity. Consequently, through suitable heating temperatures for suitable periods of time at suitable pH, suitable protein concentration and suitable stabilizer, the non-specific complement activity can be diminished in the IgM-enriched, IgG immunoglobulin concentrate product while retaining the antigenic determinants, specific antigen binding sites, specific complement activity when bound to antigen (opsonophagocytic activity) and therapeutic integrity of pdIgM, IgG immunoglobulin concentrates product.

Given the above disclosure, it is thought that variations will occur to those skilled in the art. Accordingly, it is intended that the above disclosure should be construed as illustrative and the scope of the invention should be limited only by the following claims.

We claim:

1. An antibody preparation comprising antibodies of the IgM type wherein said antibodies of the IgM type comprise at least about 20% by weight of the total amount of antibodies the preparation having the characteristics of generating non-specific complement activation of less than about 1.0 ug/ml $C4_a$ in an in vitro assay while being capable of generating specific complement activating activity.

2. In an antibody preparation comprising biologically active antibodies of the IgM and IgG types, the improvement comprising the characteristics of (A) comprising IgM antibodies in an amount of at least about 20% by weight of the total amount of antibodies;

(B) generating non-specific complement activation of less than about 1.0 ug/ml C4a in an in vitro assay, and (C) retaining antigen binding and specific complement activating activity.

3. The preparation of claim 5 wherein the IgM comprises at least about 30% by weight of the total amount of antibodies.

4. The preparation of claim 2 wherein the non-specific complement activation is shown by minimal hypotension (less than 10% reduction in arterial pressure from control) in a non-human primate test.

5. The preparation of claim 2 wherein at least 50% by weight of the IgM is biologically active and, in an in vitro assay, the preparation generates less than about 1.0 µg/ml $C4_a$.

* * * * *